US00PP32419P2

(12) United States Plant Patent
Wood

(10) Patent No.: US PP32,419 P2
(45) Date of Patent: Nov. 3, 2020

(54) ***TAXUS* PLANT NAMED 'SMNTHDB'**

(50) Latin Name: ***Taxus* x *media***
Varietal Denomination: SMNTHDB

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 16/602,660

(22) Filed: Nov. 18, 2019

(51) Int. Cl.
*A01H 7/00* (2006.01)

(52) U.S. Cl.
USPC ..... Plt./215

(58) Field of Classification Search
USPC ..... Plt./215
CPC ..... A01H 7/00
See application file for complete search history.

*Primary Examiner* — June Hwu
(74) *Attorney, Agent, or Firm* — C. A. Whealy

(57) ABSTRACT

A new and distinct cultivar of *Taxus* plant named 'SMNTHDB', characterized by its compact, overall ball-shaped plant form; freely branching habit requiring minimal pruning; dense and bushy appearance; bright green-colored leaves that maintain color throughout the seasons; and good landscape performance and hardiness.

2 Drawing Sheets

Figure 1:
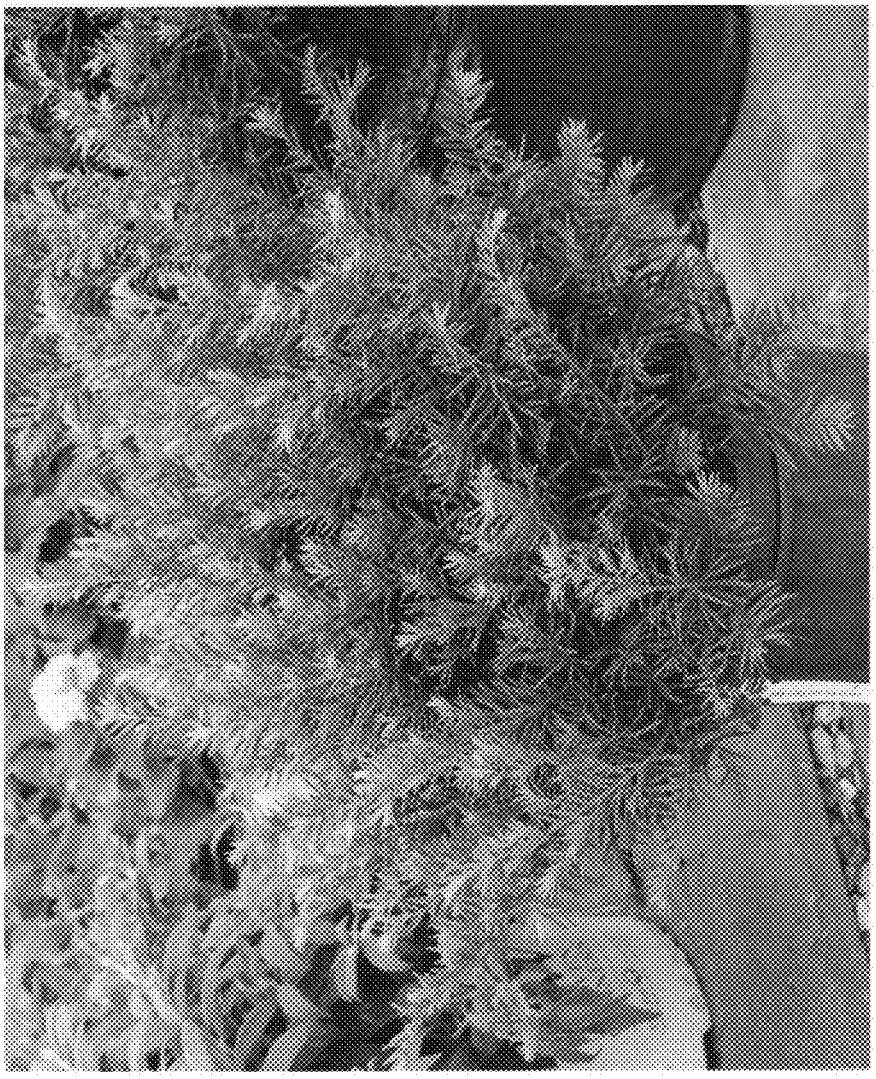

Botanical designation: *Taxus* x *media*.
Cultivar denomination: 'SMNTHDB'.

CROSS-REFERENCED IN CLOSELY-RELATED APPLICATIONS

Title: *Taxus* Plant Named 'SMNTHDPF'
Applicant: Timothy D. Wood
Filed: Concurrently with this application (U.S. Plant patent application Ser. No. 16/602,661)

BACKGROUND OF THE INVENTION

The present Invention relates to a new and distinct cultivar of *Taxus* plant, botanically known as *Taxus* x *media*, and hereinafter referred to by the name 'SMNTHDB'.

The new *Taxus* plant is a product of a planned breeding program conducted by the Inventor in Grand Haven, Mich. The objective of the breeding program was to create new *Taxus* plants with unique and attractive plant forms.

The new *Taxus* plant originated from an open-pollination in 2006 in Grand Haven, Mich. of *Taxus* x *media* 'Hicksii', not patented, as the female, or seed, parent with an unknown selection of *Taxus* x *media* as the male, or pollen, parent. The new *Taxus* plant was discovered and selected by the Inventor as a single plant from within the progeny of the stated open-pollination in a controlled environment in Grand Haven, Mich. in 2011.

Asexual reproduction of the new *Taxus* plant by softwood stem cuttings taken in a controlled environment in Grand Haven, Mich. since 2011 has shown that the unique features of this new *Taxus* plant are stable and reproduced true to type in successive generations.

SUMMARY OF THE INVENTION

Plants of the new *Taxus* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'SMNTHDB'. These characteristics in combination distinguish 'SMNTHDB' as a new and distinct cultivar of *Taxus* plant:

1. Compact, overall ball-shaped plant form.
2. Freely branching habit requiring minimal pruning; dense and bushy appearance.
3. Bright green-colored leaves that maintain color throughout the seasons.
4. Good landscape performance and hardiness.

Plants of the new *Taxus* can be compared to plants of the female parent, 'Hicksii', in plant size as plants of the new *Taxus* are more compact than plants of 'Hicksii'.

Plants of the new *Taxus* can be compared to plants of *Taxus* x *media* 'SMNTHDC', disclosed in U.S. Plant Pat. No. 31,795. Plants of the new *Taxus* differ primarily from plants of 'SMNTHDC' in the following characteristics:

1. Overall shape of plants of the new *Taxus* is ball-shaped whereas overall shape of plants of 'SMNTHDC' is columnar.
2. Leaves of plants of the new *Taxus* are bright green in color whereas leaves of plants of 'SMNTHDC' are darker green in color.

Plants of the new *Taxus* can also be compared to plants of *Taxus* x *media* 'SMNTHDPF', disclosed in U.S. Plant Patent application filed concurrently, in plant shape as overall shape of plants of the new *Taxus* is ball-shaped whereas overall shape of plants of 'SMNTHDPF' is columnar.

BRIEF DESCRIPTION OF THE PHOTOGRAPHS

The accompanying colored photographs illustrate the overall appearance of the new *Taxus* plant showing the colors as true as it is reasonably possible to obtain in colored reproductions of this type. Colors in the photographs may differ slightly from the color values cited in the detailed botanical description which accurately describe the colors of the new *Taxus* plant.

The photograph on the first sheet (FIG. 1 of 2) is a side perspective view of a typical plant of 'SMNTHDB' grown in a container in a polyethylene-covered greenhouse environment in Grand Haven, Mich.

Figure 2:
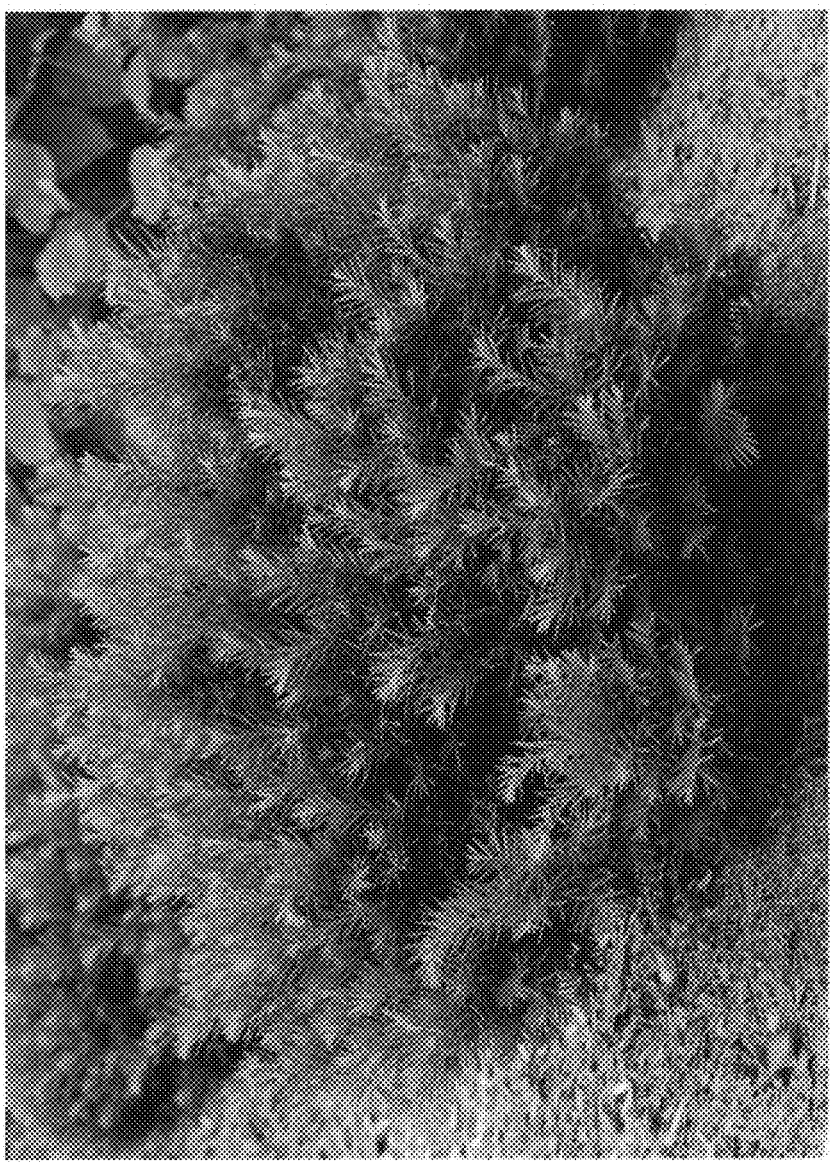

The photograph on the second sheet (FIG. 2 of 2) is a side perspective view of a typical plant of 'SMNTHDB' grown in an outdoor nursery in Grand Haven, Mich. Plants used for the photographs were three years old.

DETAILED BOTANICAL DESCRIPTION

Plants used for the following observations and measurements were grown during the summer in five-gallon containers in a polyethylene-covered greenhouse in Grand Haven, Mich. Plants were grown under cultural practices typical of commercial *Taxus* plant production. During the production of the plants, day temperatures ranged from 18° C. to 27° C. and night temperatures ranged from 5° C. to 10° C. Plants were two years old when the description was taken. In the following description, color references are made to The Royal Horticultural Society Colour Chart, 2015 Edition, except where general terms of ordinary dictionary significance are used.

Botanical classification: *Taxus* x *media* 'SMNTHDB'.

Parentage:

*Female, or seed, parent*.—*Taxus* x *media* 'Hicksii', not patented.

*Male, or pollen, parent*.—Unknown selection of *Taxus* x *media*, not patented.

Propagation:

*Type*.—By softwood stem cuttings.

*Time to initiate roots*.—About one month at temperatures about 18° C. to 27° C.

*Time to produce a rooted cutting*.—About three months at temperatures about 18° C. to 27° C.

*Root description*.—Thick, fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant form and growth habit*.—Perennial evergreen shrub; relatively compact, upright to outwardly spreading and mounding, overall ball-shaped plant form; moderately vigorous growth habit and moderate growth rate.

*Branching habit*.—Freely branching habit requiring minimal pruning; dense and bushy appearance; about 20 to 50 lateral branches developing per plant.

*Plant height*.—About 47 cm.

*Plant diameter*.—About 59 cm.

*Lateral branch description*.—Length: About 31 cm. Diameter: About 5 mm. Internode length: About 5 mm. Strength: Strong, flexible. Aspect: About 15° to 60° from vertical. Texture: Smooth, glabrous. Color, developing: Close to 143A. Color, mature: Close to 174B.

*Leaf description*.—Arrangement: Alternate, simple. Length: About 3 cm. Width: About 3 mm. Shape: Acicular. Apex: Cuspidate. Base: Oblique. Margin: Entire. Texture, upper and lower surfaces: Smooth, glabrous. Venation pattern: Parallel. Color: Developing leaves, upper and lower surfaces: Close to 144C. Fully expanded leaves, upper surface: Close to 139A; venation, close to 139A; leaf color is maintained throughout the seasons. Fully expanded leaves, lower surface: Close to 143A; venation, close to 143A; leaf color is maintained throughout the seasons. Petioles: Length: About 1 mm. Diameter: About 1 mm. Texture, upper and lower surfaces: Smooth, glabrous. Color, upper and lower surfaces: Close to 144B.

*Flower description*.—To date, flower development has not been observed on plants of the new *Taxus*.

Pathogen & pest resistance: To date, plants of the new *Taxus* have not been observed to be resistant to pathogens or pests common to *Taxus* plants.

Landscape performance: Plants of the new *Taxus* have been observed to have good landscape performance and to be tolerant temperatures ranging from about −32° C. to about 36° C.

It is claimed:

1. A new and distinct *Taxus* plant named 'SMNTHDB' as illustrated and described.

* * * * *